(12) United States Patent
Soumillion et al.

(10) Patent No.: US 6,969,593 B2
(45) Date of Patent: Nov. 29, 2005

(54) METHOD FOR THE SELECTIVE SURVIVAL OR SELECTIVE GROWTH OF A TARGET CELL BY THE USE OF A CONJUGATE, ITS USE IN THERAPEUTICS AND/OR DIAGNOSTICS AND THE PREPARATION OF SAID CONJUGATE

(75) Inventors: Patrice Soumillion, Brussels (BE); Jacques Fastrez, Perwez (BE)

(73) Assignee: Universite Catholique de Louvain, Louvain-la-Neuve (BE)

( * ) Notice: Subject to any disclaimer, the term of this patent is extended or adjusted under 35 U.S.C. 154(b) by 15 days.

(21) Appl. No.: 10/311,786

(22) PCT Filed: Jun. 7, 2001

(86) PCT No.: PCT/EP01/06439
§ 371 (c)(1),
(2), (4) Date: Dec. 18, 2002

(87) PCT Pub. No.: WO01/97854
PCT Pub. Date: Dec. 27, 2001

(65) Prior Publication Data
US 2003/0099658 A1 May 29, 2003

(30) Foreign Application Priority Data
Jun. 21, 2000 (EP) .............................. 00870139

(51) Int. Cl.⁷ .......................... C12Q 1/04; C12P 21/08; A61K 39/395; A01N 37/18; G01N 33/53
(52) U.S. Cl. ................... 435/34; 530/388.2; 530/387.3; 530/388.5; 530/391.7; 435/18; 435/231; 435/7.1; 435/252.1; 435/260; 435/38; 514/2; 424/178.1
(58) Field of Search ............................ 435/231, 18, 7.1, 435/252.1, 260, 34, 38; 530/387.3, 388.2, 388.5, 391.7; 514/2; 424/178.1

(56) References Cited
FOREIGN PATENT DOCUMENTS

WO WO 97/34634 A1 9/1997
WO WO 98/56425 A1 12/1998

OTHER PUBLICATIONS

Witkowski et al. , Biochemistry 38:11643–11650, 1999.*
Seffernick et al. , J. Bacteriol. 183(8):2405–2410, 2001.*
Kerr et al. , Bioconjugate Chemistry 10:1084–1089, 1999.*
Meyer et al., Preparation and characterization of a beta–lactamase Fab' conjugate for the site–specific activation of oncolytic acents, Bioconjug Chem 3(1): 42–48 (1992).
American Type Culture Collection, Catalogue of Filamentous Fungi, 1991, p 55, Rockville, Maryland.
American Type Culture Collection, Catalogue of Bacteria and Phages. 1992. p. 279. Rockville, Maryland.

* cited by examiner

Primary Examiner—Rebecca E. Prouty
Assistant Examiner—Delia M. Ramirez
(74) Attorney, Agent, or Firm—Amster, Rothstein & Ebenstein LLP

(57) ABSTRACT

The invention is in particular related to a method for the selective survival or selective growth of a target cell comprising the steps of: a) contacting the target cell with a conjugate compound A-B, wherein A is a selective antibody or antibody derivative recognizing the target cell and B is a biotic agent able to at least partially inactivate an anti-bios agent, said anti-bios agent is able to inhibit the growth of cells; and b) contacting the target cell with the anti-bios agent. The present invention also relates to said conjugate on its own, a selection medium for cells comprising said conjugate and cells that are selected or recognized using a method or conjugate according to the present invention. The present invention further elucidates a pharmaceutical compound or composition, a kit for the detection of a target cell or for the diagnosis of diseases caused by the target cell or a product that can be used in the therapy of infectious related diseases comprising a conjugate according to present invention.

26 Claims, 10 Drawing Sheets

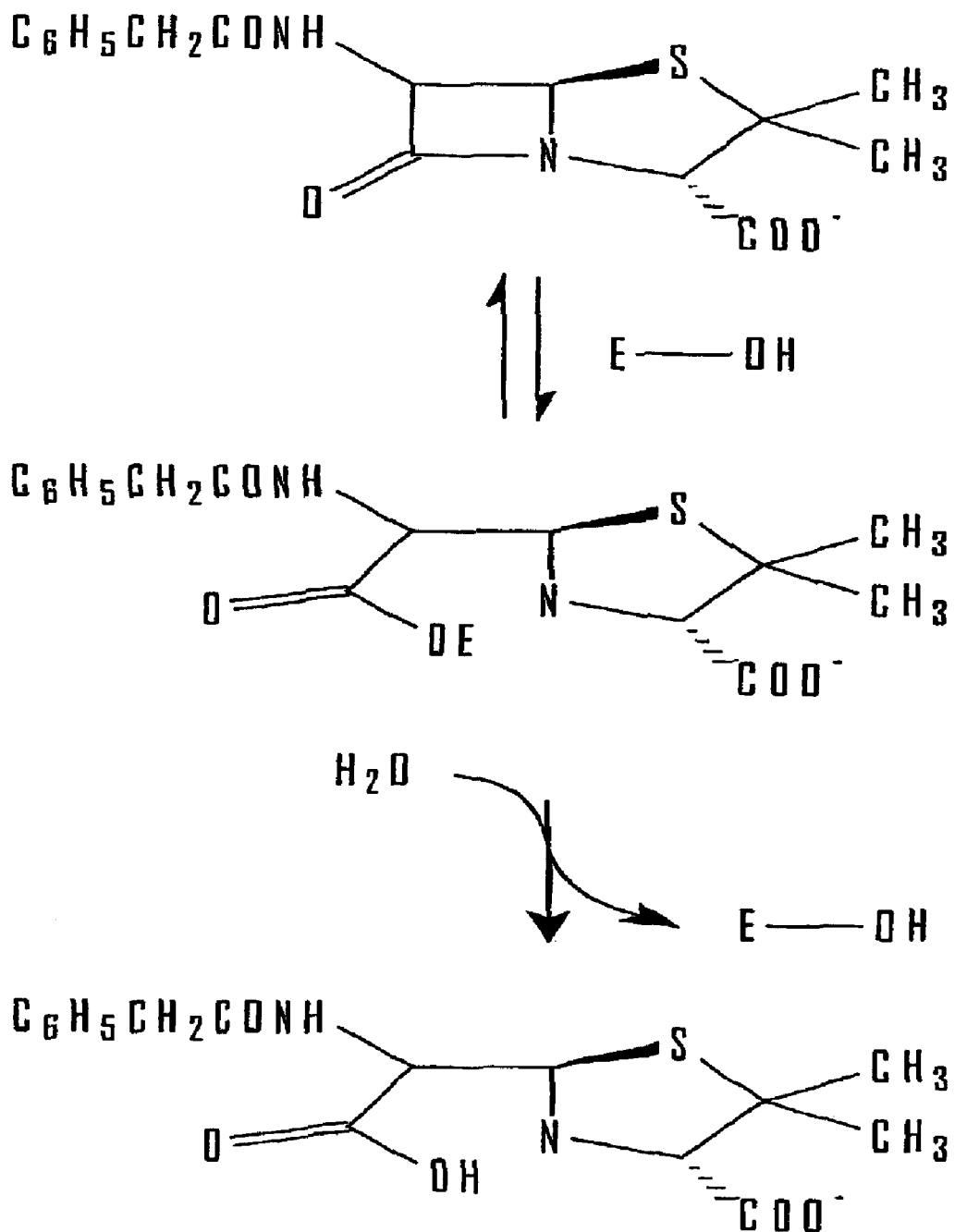

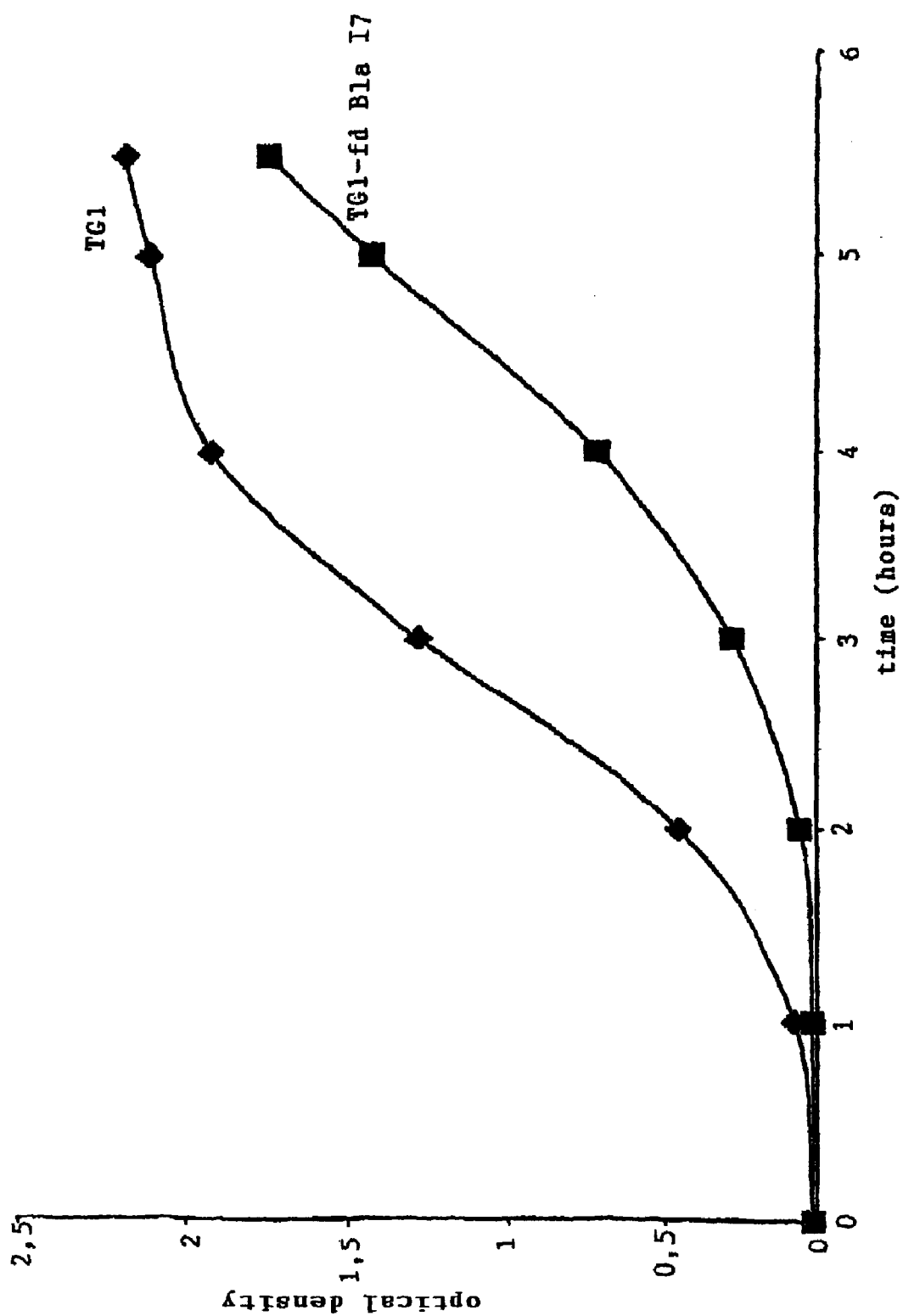
Figure 2: Growing curves of TG1 and TG1-fd Bla I7.

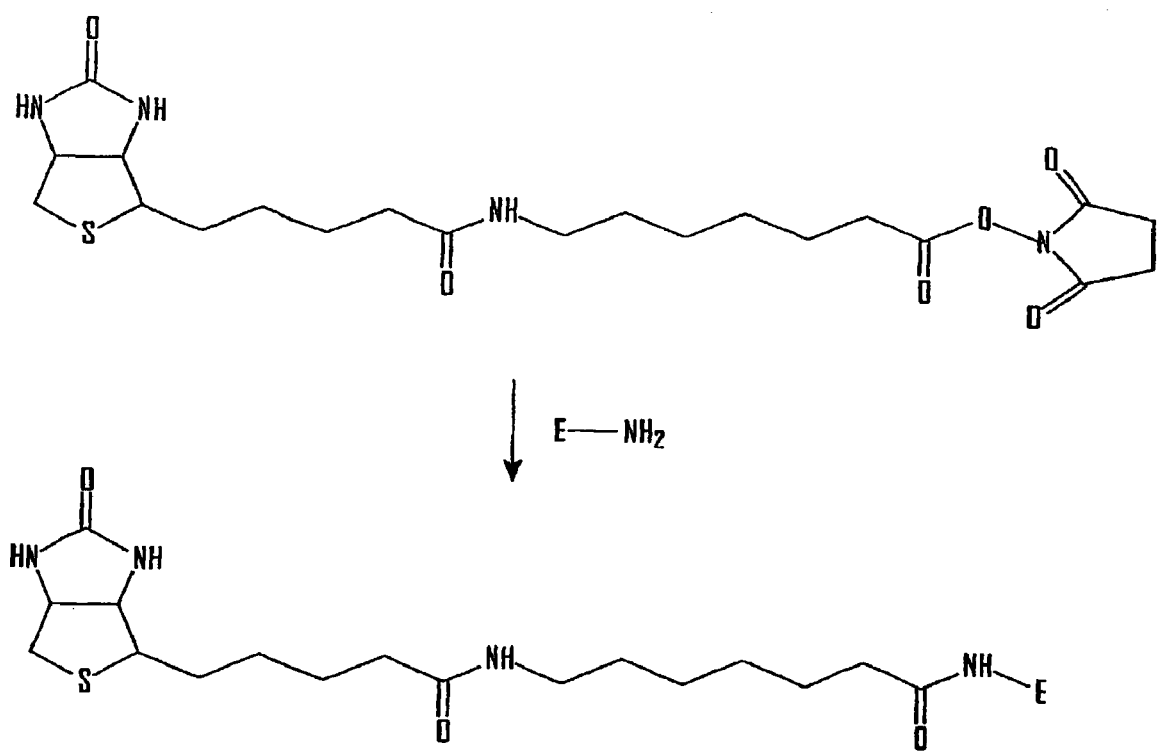
Figure 3: Reaction of biotinylation

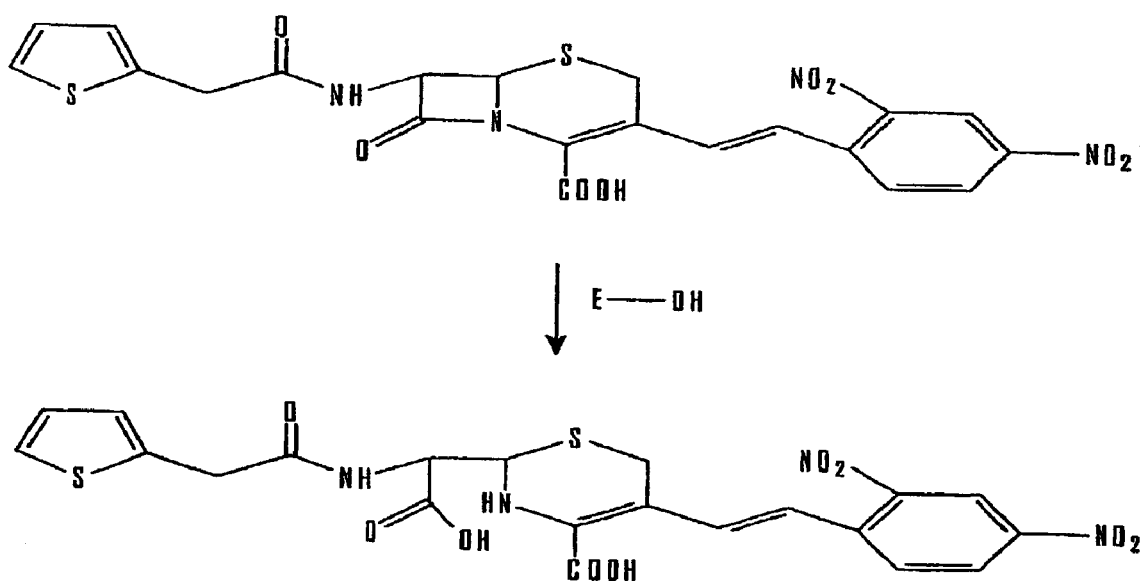
Figure 4: Reaction of hydrolysis of nitrocefine by β-lactamase

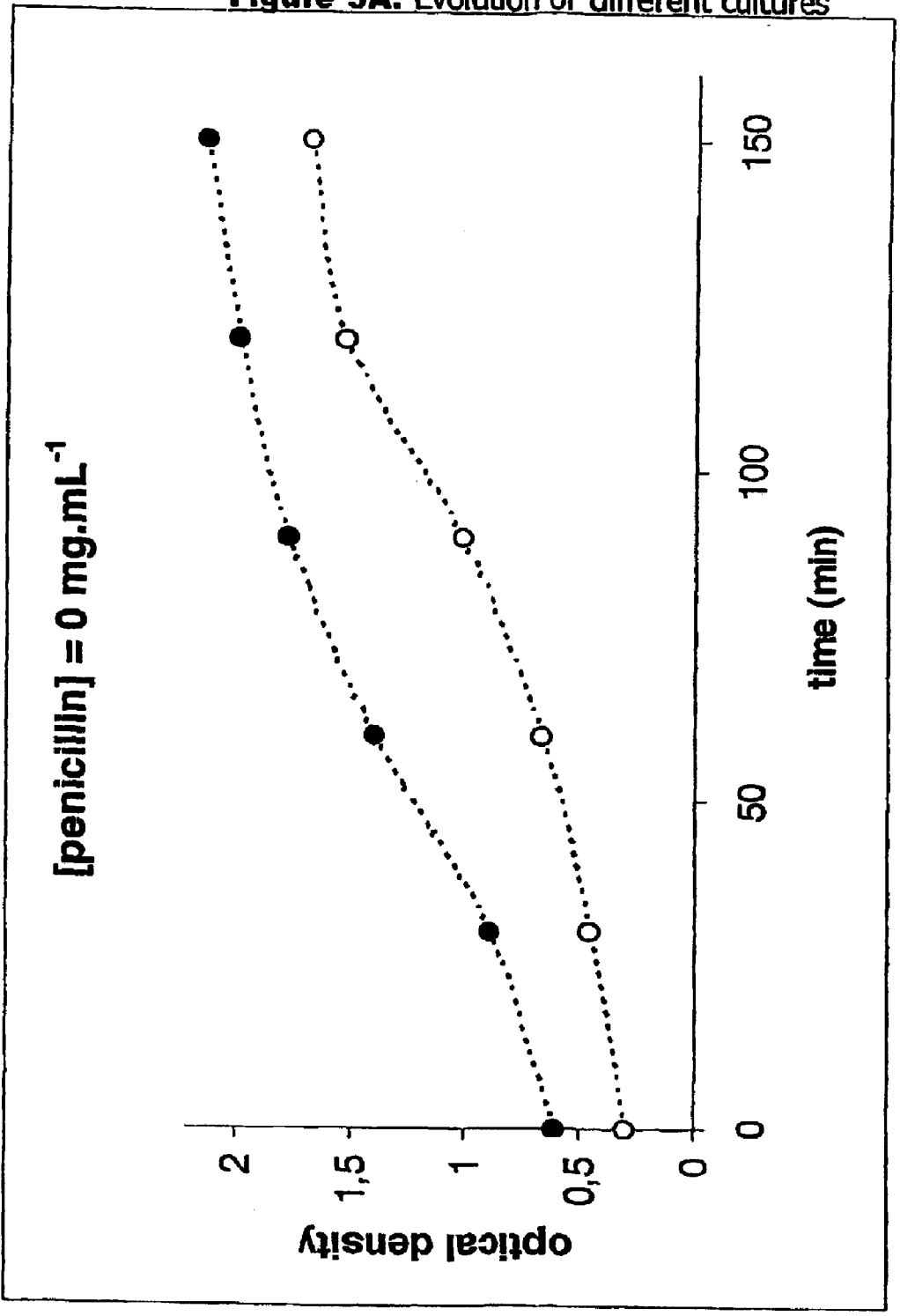
Figure 5A: Evolution of different cultures
Legend: full circles : MM294-pET26b45
open circles : TG1-fd Bla I7
full line : with ternary complex (conjugate A-B)
dotted line : without ternary complex (conjugate A-B)

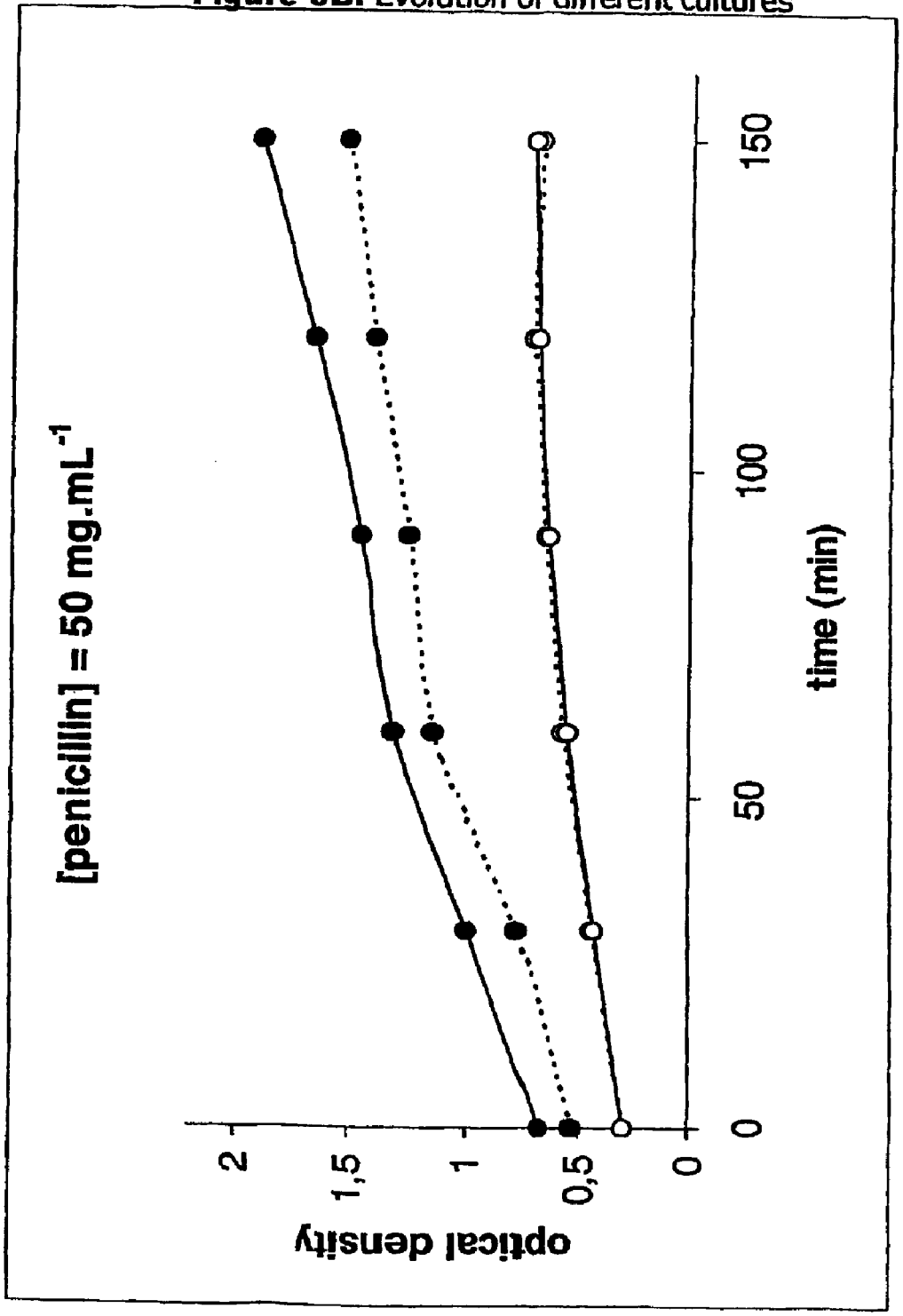
Figure 5B: Evolution of different cultures
Legend: full circles : MM294-pET26b45
open circles : TG1-fd Bla I7
full line : with ternary complex (conjugate A-B)
dotted line : without ternary complex (conjugate A-B)

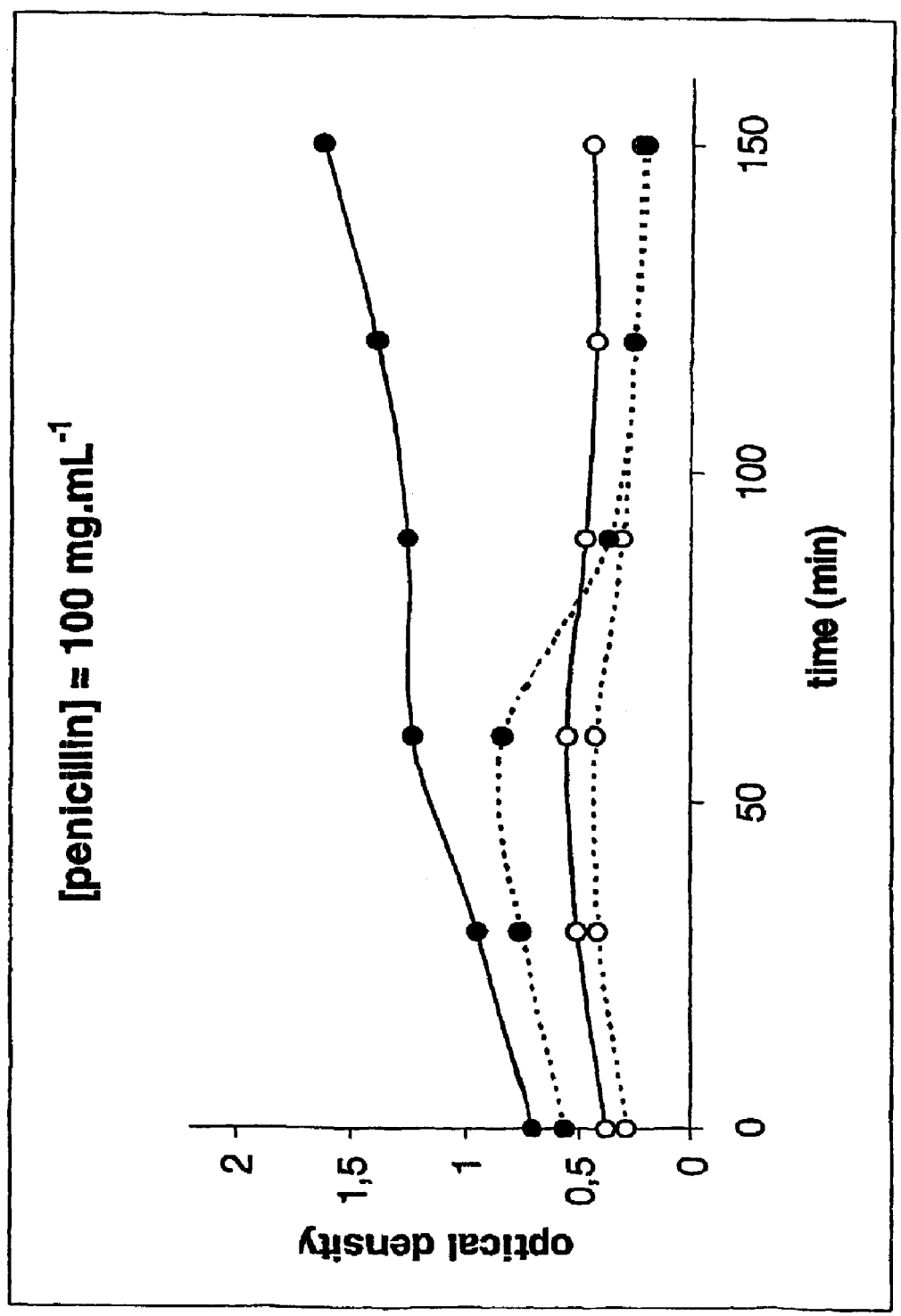
Figure 5C: Evolution of different cultures
Legend: full circles : MM294-pET26b45
open circles : TG1-fd Bla I7
full line : with ternary complex (conjugate A-B)
dotted line : without ternary complex (conjugate A-B)

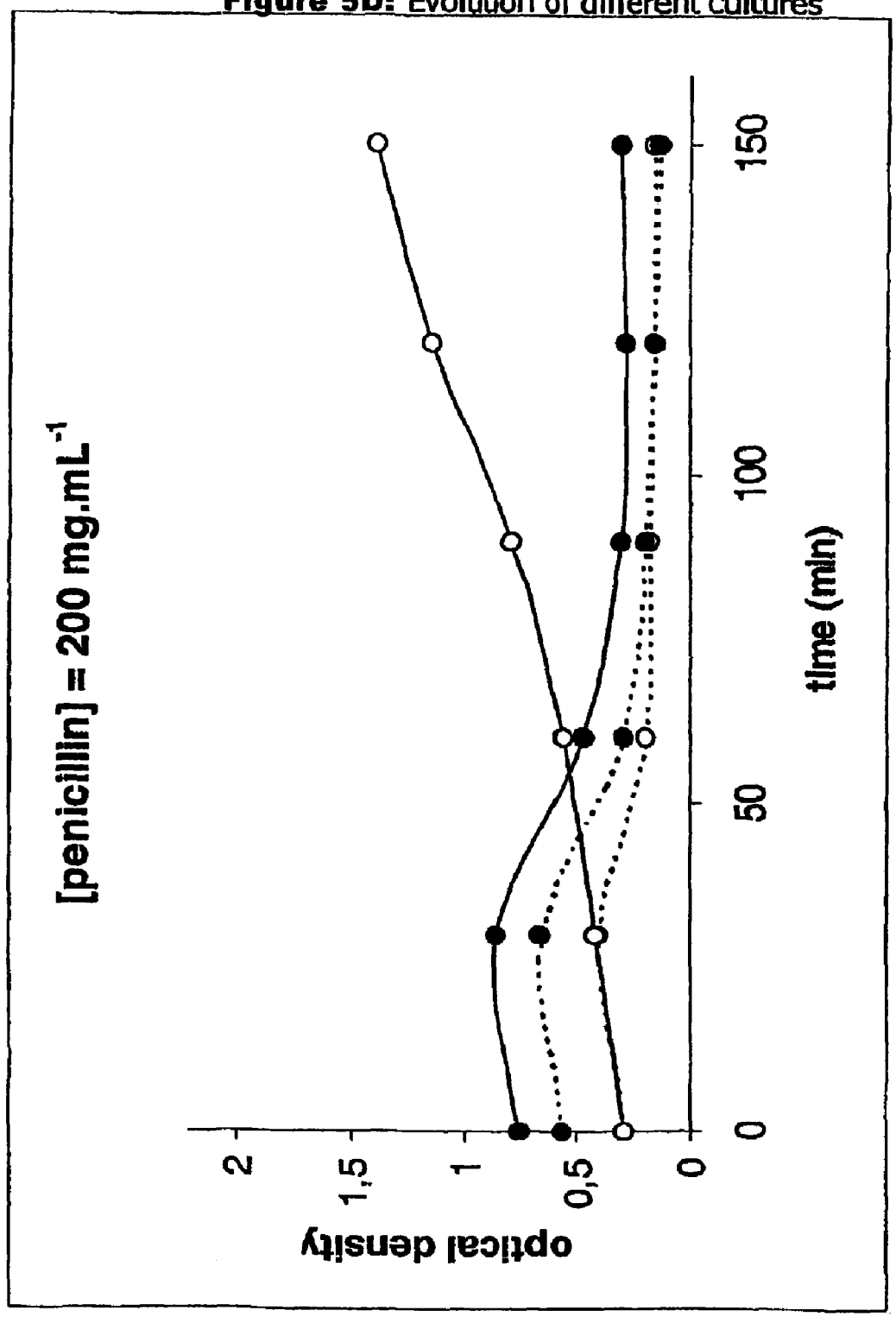
Figure 5D: Evolution of different cultures
Legend: full circles : MM294-pET26b45
open circles : TG1-fd Bla I7
full line : with ternary complex (conjugate A-B)
dotted line : without ternary complex (conjugate A-B)

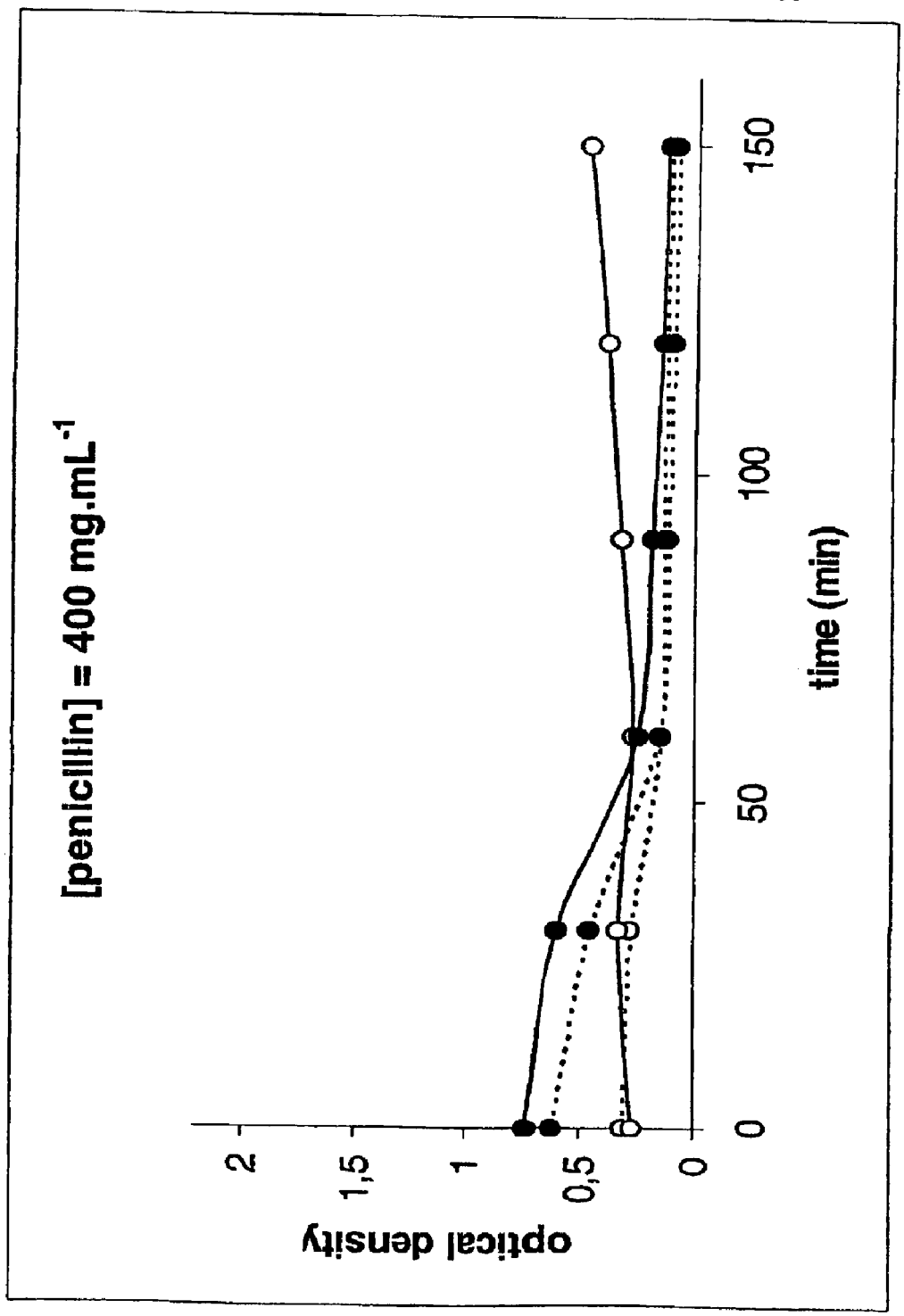
Figure 5E: Evolution of different cultures
Legend: full circles : MM294-pET26b45
open circles : TG1-fd Bla I7
full line : with ternary complex (conjugate A-B)
dotted line : without ternary complex (conjugate A-B)

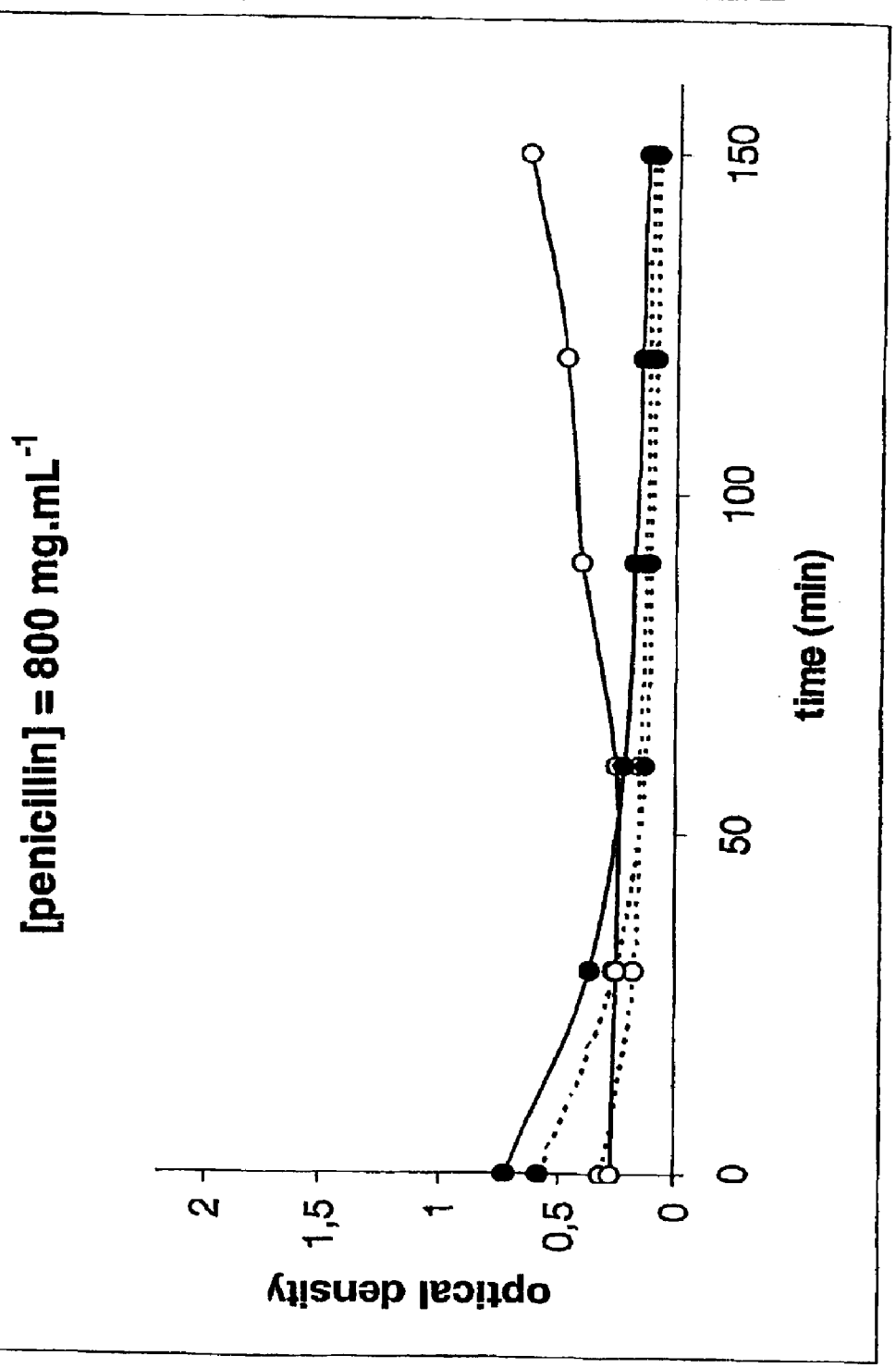
Figure 5F: Evolution of different cultures
Legend: full circles : MM294-pET26b45
open circles : TG1-fd Bla I7
full line : with ternary complex (conjugate A-B)
dotted line : without ternary complex (conjugate A-B)

METHOD FOR THE SELECTIVE SURVIVAL OR SELECTIVE GROWTH OF A TARGET CELL BY THE USE OF A CONJUGATE, ITS USE IN THERAPEUTICS AND/OR DIAGNOSTICS AND THE PREPARATION OF SAID CONJUGATE

This application is a 35 U.S.C. 371 National Stage application of PCT/EP01/06439, published in English under PCT Article 21(2), and claiming the benefit of European Application 00870139.3, filed Jun. 21, 2000. The above applications are incorporated by reference in their entirety.

TECHNICAL FIELD

The present invention relates to a novel method for an improved detection, selection, isolation, targeting and/or inhibiting or improving the growth of target cells in particular a method for the selective survival or selective growth of a target cell by the use of a conjugate, their use in therapeutics and diagnostics and the preparation of said conjugate. In the present invention the wording selection comprises selective survival and/or selective growth.

BACKGROUND ART

Food is considered to favor growth of unwanted cells such as bacteria, yeast, and fungi. In general non-pathogenic bacteria are considered as having no negative consequence for human health. Several are even known to have beneficial effects on our organism, for example L-caseT-Immunitas which facilitate the intestinal transit. However, several pathogenic bacteria such as *Salmonella* and *Listeria* are capable to grow fast in rich environments such as food. In the last decades serious health problems are frequently arising caused by these contaminating cells. Therefore many efforts have been made to find tools to detect these contaminations before the food is distributed on the market.

In general, strategies for the characterisation of bacterial and/or other contamination consists of a two-step method:
  the first step involves the amplification, i.e. a bacterial multiplication in a sample of the food suspension to be analyzed,
  the second step involves the detection, i.e. the proof of the presence of pathogenic bacteria.

The total absence or the minor presence (a non-toxic dosis) of the pathogenic bacteria will allow a safe consumption of the respective food.

If the amplification is done in a rich culture medium all bacteria or cells present in the sample will grow. This step is not specific and may result in a severe miscalculation of the pathogenic bacteria. Indeed, a non-selective medium will amplify all the cells in the sample, including the target cells, and the subsequent detection will be much more laborious and less reliable.

In order to solve this known problem it is of importance to have an amplification which is performed selectively resulting in the enrichment of the cell which needs to be detected in the second step. Consequently, methods have been developed using a specific medium comprising specific growth factors allowing the growth of only the cell which one need to detected lateron. This is performed by optimising culture conditions to favor the target cells growth and disfavor all the other cell growths. For each cell type a specific temperature, medium and time of incubation is chosen. In general, the required culture time will be short if the medium is rich but allowing all present cells to grow. Unfortunately, these methods need an extensive input to optimize time of incubation and selectivity of the medium wherein the target cell grows faster compared to the growth of background cells. Some selective media have been developed by optimizing their composition but they are usually poor selective and/or poor nutritive. In the latter case, the time of incubation need to be extended.

However, these methods have a serious inconvenience: by increasing the specificity of a medium the nutritional elements will be provided in at much lower concentration resulting in a considerable decrease of the growth rate of the bacteria in this medium. Indeed, samples which are taken from food for rapid consumption need to be evaluated quickly for the presence of pathogenic organisms. Because enterprises can not allow a slow process for analysis one need a specific and fast identification method for contaminating and/or pathogenic cells. In addition, the extensive investment to select, determine such a medium and the time needed for cultivation is a major drawback of this approach.

There is a lot of literature concerning selective enrichment media used for the detection of pathogenic bacteria in food (see de Boer E: Update on media for isolation of enterobacteriaceae from foods. *International Journal Of Food Microbiology* 1998, 45: 43–53). To our knowledge, nothing similar to our project has ever been done. In general, the broth's composition is adapted to the metabolism of the target bacteria (see Altwegg M, Buser J, Vongraevenitz A: Stool cultures for *shigella* spp: improved specificity by using macconkey agar with xylose. *Diagnostic Microbiology And Infectious Disease* 1996, 24: 121–124) or a toxic compound, for which the target bacteria is less sensitive than most of the other bacteria, is added (see Chen H, Fraser A D E, Yamazaki H: Evaluation of the toxicity of *salmonella* selective media for shortening the enrichment period. *International Journal Of Food Microbiology* 1993, 18: 151–159). The major problem of these media is the slow growth rate or the difficulty to obtain together the high selectivity and the high growth rate.

A well known DNA amplification technique called PCR (polymerase chain reaction) is also used to detect a genetic signature of a target pathogenic bacterium in samples containing very small amount of microorganisms (see Fluit A C, Widjojoatmodjo M N, Box A T A, Torensma R, Verhoef J: Rapid detection of salmonellae in poultry with the magnetic immuno-polymerase chain-reaction assay. *Applied And Environmental Microbiology* 1993, 59: 1342–1346; Olsen J E, Aabo S, Hill W, Notermans S, Wernars K, Granum P E, Popovic T, Rasmussen H N, Olsvik O: Probes and polymerase chain-reaction for detection of food-borne bacterial pathogens international. *Journal Of Food Microbiology* 1995, 28: 1–78.). The need to selectively grow the bacteria before the detection itself is less imperative here. Nevertheless, an enrichment culture is always obligatory and the detection procedure (PCR followed by electrophoresis analysis) is time consuming and necessitates specialized technician and equipment.

An alternative method based on immunoseparation is also used (see Blackburn C D: Rapid and alternative methods for the detection of *salmonellas* in foods. *Journal Of Applied Bacteriology* 1993, 75: 199–214; Mansfield L P, Forste S J: Immunomagnetic separation as an alternative to enrichment broths for *salmonella* detection. *Letters In Applied Microbiology* 1993, 16: 122–125). Magnetic beads coated with an antibody that recognizes the target bacteria allow to specifically separate the bacteria from a pre-enriched culture. Apparently, the method is rapid but there could be some problems with the separation step which is avoided in our strategy.

BRIEF DESCRIPTION OF THE SEVERAL VIEWS OF THE DRAWINGS

FIG. 1: Hydrolized reaction of penicilline by β-lactainase.

FIG. 2: Growing curves of TG1 and TG1-fd Bla I7.

FIG. 3: Reaction of biotinylation.

FIG. 4: Reaction of hydrolyzed nitrocefine by β-lactamase.

FIG. 5: Evolution of different cultures. Panel A: penicillin concentration=0 mg mL$^{-1}$; Panel B: penicillin concentration=50 mg mL$^{-1}$; Panel C: penicillin concentration=100 mg mL$^{-1}$; Panel D: penicillin concentration=200 mg mL$^{-1}$; Panel E: penicillin concentration=400 mg mL$^{-1}$; Panel F: penicillin concentration=800 mg mL$^{-1}$.

DETAILED DESCRIPTION OF THE INVENTION

The main object of the present invention is to provide a fast and selective method for the detection, selection, isolation, targeting and allowing survival or improving the growth of target cells which can be present in complex solutions.

In a first aspect the present invention provides therefor a method for the selection of a target cell comprising the steps of: a) contacting the target cell with a conjugate compound A-B, wherein A is a selective antibody or antibody derivative recognizing the target cell and B is a biotic agent able to at least partially inactivate an anti-bios agent, said anti-bios agent is able to inhibit the growth of cells; and b) contacting the target cell with the anti-bios agent.

According to the invention, it is possible to selectively protect target cells against an anti-bios agent which is able to unfavour the growth of a large number of cell types cells in specific conditions thereby making it possible to make a fast selection of specific target cells.

Under selection of a target cell is meant that target cells can be detected, targeted, grown and/or isolated selectively, within or from a cell environment such as cell suspension comprising two or more different cell types. The selectivity is determined by the selective character of the antibody in recognising the target cell compared to the cross reactivity of this antibody towards other non-target cells. Said antibody recognises an extracellular component of the cell that is part of the cell membrane or a cell wall that surrounds the cell. Bacterial cells are surrounded by a complex structure comprising one or two membranes; peptidoglycan, lipopolysaccharrides, lipotechoic acids, anchored and membrane proteins and sometimes S-layer. Eucaryotic cells are usually only surrounded by a membrane harbouring a variety of biomolecules such as glycoproteins, receptors, lipids. For all cell types, some of these external components are only present on specific cells and are an ideal target to choose the antibody to. Indeed, the more unique the epitope recognised by the antibody is, the lower the cross reactivity of the antibody will be on non-target cells; consequently, the more selective the selection of the target cells will be. Antibodies used according to the present invention can be monoclonal or polyclonal, capable of binding specifically to one or more epitopes of the extracellular proteins. The antibodies according to the invention may be produced according to techniques which are known to those skilled in the art. Monoclonal antibodies may be prepared using conventional hybridoma technology as described by Kohler and Milstein (1979) (Kohler, F. and Milstein, C. 1995. Continuous cultures of fused cells secreting antibody of predefined specificity. Nature 256: 495–497.). Polyclonal antibodies may also be prepared using conventional technology well known to those skilled in the art, and which comprises inoculating a host animal, such as mouse, with a protein or epitope as described above and recovering the immune serum. The antibodies used according to the present invention may also consist of a fragment or fragments of whole antibodies which maintain their binding activity, such as for example, Fv, F(ab') and F(ab')2 fragments as well as single chain antibodies. The target cell to be selected can be of prokaryotic or of eukaryotic (higher or lower) origin, pathogenic or non-pathogenic, normal or mutated cells. The cell environment for example the cell suspension from which the target cell needs to be isolated can be of diverse origin such as food, waste, soil and body fluids. A biotic agent is herein defined as an agent which enables a cell to survive in a condition where an anti-bios agent is present. So, the biotic-agent allows a cell to be protected due to its ability to partially or complete inactivate the anti-biotic agent. The anti-bios agent acts on one or more essential pathway(s) of the cell which is essential for survival and its activity results in the decrease or inhibition of cell growth. The antibody as described in the present invention is linked to the biotic agent via a covalent or non-covalent bound as described below.

According to the present invention, the addition of the A-B conjugate and the anti-bios agent to the cell environment can be performed simultaneously. In this way, for example a premix containing both compounds can be made on beforehand resulting in the decrease of the number of manipulation steps necessary to perform during the method and time can be saved. In cases the anti-bios agent can be inactivated by the biotic complex when present in the same solution, the premix will be made just before the experiment is started. In case the biotic agent is not able to inactivate the anti-bios directly, the premix may be made longer in advance. Alternatively and preferably according to the method of the invention, the A-B and the anti-bios agent can be added sequentially: A-B complex can be added to the cell suspension subsequently followed by the addition of the anti-bios agent. Using this strategy, cells are first protected and then challenged to an anti-bios agent.

According to the present invention the target cell is selected from a mixture of cells. By the addition of the biotic agent, the target cell is made resistant to the activity of the anti-bios activity. Protected or resistant cells resist the described challenge, contrarily, non-target cells will be restricted in their metabolic conditions resulting in the reduction or inhibition of growth. The anti-bios compound can have static and/or cidal activity, resulting in the inhibition of cell growth and/or killing of the cells. The anti-bios compound may be chosen in such a way that is has a broad spectrum in inhibiting or killing most and preferably all cells present in the cell environment except the target cells which are able to bind the A-B complex.

In case the concentration at which target cells are present in the cell environment is low, target cells need to be cultivated. If not, signals obtained by known methods will be too low and the contaminating target cells will not be detected. Preferentially, the methods according to the present invention involve an amplification step which is necessary in order to have sufficient target cells for example bacteria for the selection. This is of prime importance as the target cells need to be detected in food. In the method as described in present invention rich medium is applied which allow a fast growth of cells, and is additionally supplemented with a specific set of compounds, which contains according to the invention at least the A-B complex and the anti-bios agent, allowing only the target, cells to amplify. In this way, fast growth is allowed for only the target cells without extensive optimization of growth conditions. During the selection condition, where the anti-bios agent is present, target cells can be cultivated. Once the target cells are in a reasonable number present these can be easily detected.

The detection of the target cells can be performed via different systems as known by a person skilled in the art. A wide variety of protocols are available but they are always based on an immunodetection strategy that can be done on a filter or a microplate well or a tip of an optical fiber. The ELISA method is such an immunodetection strategy, well known for a person skilled in the art.

According to the present invention the method for the selection of a target cell from a mixture of cells may comprise the steps of: a) identifying a selective antibody or antibody derivative A recognizing the target cell. The more unique the epitope recognised by the antibody is, the lower the cross reactivity of the antibody will be in recognising non-target cells; consequently, the more selective the selection of the target cells will be. Said antibody or antibody derivative A preferentially recognises an extracellular component of the cell that is part of the cell membrane or a cell wall that surrounds the cell. Bacterial cells are surrounded by a complex structure comprising one or two membranes, peptidoglycan, lipopolysaccharrides, lipotechoic adds, anchored and membrane proteins and sometimes S-layer. Eucaryotic cells are usually only surrounded by a membrane harbouring a variety of biomolecules such as glycoproteins, receptors, lipids. For all cell types, some of these external components are only present on specific cells and are an ideal target to choose the antibody to. In some cases this epitope only present on specific cells may be known from prior art documents and antibodies recognising these may be commercial available or can be obtained from third parties. In other cases, epitopes might be known, but corresponding antibodies will have to be made. This can be achieved using standard techniques known by a person skilled in the art.

Additionally, an anti-bios agent needs to be identified able to inhibit the growth of cells present in the cell environment and is described as step b in a preferred embodiment. The anti-bios agent acts on one or more essential pathways of the cell which is essential for survival and its activity results in the decrease or inhibition of cell growth. The anti-bios compound can have static and/or cidal activity, resulting in the inhibition of cell growth and/or killing of the cells. The anti-bios compound is chosen in such a way that is has a broad spectrum in inhibiting growth or killing cells present in the cell environment except the target cells which were able to bind the A-B complex. The anti-bios is chosen depending on the type of organisms that are present in the cell suspension. In most cases, a prediction can be made. For example, if the suspension contains bacteria, the anti-bios will be a β-lactam antibiotic such as ampicillin or an aminoglycoside which have a broad spectrum against bacterial strains. These assumptions can be experimentally confirmed: first one need to analyse if all cells are inhibited using the anti-bios agent, secondly genetically transformed target cells carrying a gene that allows the production of the biotic agent can be subjected to the anti-bios compound and tested if the biotic agent allows to inhibit the added anti-bios agent. For the person skilled in the art, it is evident once the anti-bios agent is chosen to assign a corresponding biotic-agent B able to at least partially inactivate the anti-bios agent.

Once the antibody (A), the biotic-(B) and the anti-bios agent is chosen, coupling of the antibody A with the biotic agent B results in a conjugate A-B. Three methods can be used to link A to B. If A and B are polypeptides and the corresponding genes are available, the simplest method is the genetic construction of a fusion gene containing the DNA coding regions of A and B linked together so that the conjugate A-B is expressed as a single polypeptide chain. Another way is to use chemical crosslinking reagents which are small bifunctional molecules that are able to make a covalent link between A and B. A third method is to chemically modify A and B with a specific group which can make a very stable association with a third partner. This third partner contains at least two binding sites for the specific group, thus allowing to fix at least one modified antibody A and one modified biotic agent B. Examples of suitable chemical reagents allowing crosslinking or modification by specific groups are given below.

Subsequently, a medium is prepared containing the conjugate A-B. As pointed out before, in the method as described in present invention the medium which is applied is a rich medium allowing fast growth of cells. This means that the essential nutrients are present in an unlimited concentration and in such a form that the organism needs low input to convert complex molecules into metabolic usable substrates. For example, Luria-Bertani medium or Terrific Broth are rich media for bacterial culture. These media contain nutrient from yeast extract and casein hydrolysate. For all cell types, rich media are available and well known for a person skilled in the art. This rich medium is additionally supplemented with a specific A-B complex composed of a specific antibody or antibody derivative A and a well-chosen biotic agent B (step d in a preferred embodiment of the present invention). A only binds the target-cell when bringing together the original cell suspension with the medium as obtained as described above (step e in a preferred embodiment of the present invention). At the moment the anti-bios agent is added to the cell-containing-medium (step e in a preferred embodiment of the present invention) directly or with a delay (see above) the cell containing mixture is incubated at an optimal temperature which is defined by the target organism. Due to the fact that most cells have their optimal temperature at 37° C., this temperature is the most preferred to be used. Some additional features are sometimes necessary, such as $CO_2$ and $O_2$ supply. These additional culture conditions are most of the time evident and conditions can be adapted as known by the person skilled in the art. Through the addition of the A-B complex, which is selective for the target cell, one allows only the target cells to amplify. In this way, fast growth is allowed for only the target cells without extensive optimization of growth conditions. During the selection condition, where the anti-bios agent is present, target cells can be cultivated as long as needed (step f in a preferred embodiment of the present invention). Once the target cells are in a reasonable number present these can be easily detected.

According to a preferred embodiment, said anti-bios agent is an antibiotic agent This agent is able to inhibit growth or kill a large number of cell types.

In the method according to present invention said antibiotic agent is chosen from the group comprising β-lactam antibiotics (penicillin, cephalosporin), chloramphenicol, aminoglycosides or derivatives thereof. β-lactam antibiotics act by inhibiting bacterial enzymes involved in the synthesis and degradation of the bacterial wall. This inhibition prevents bacterial division and is the origin of the bacteriostatic and bactericidal effects of β-lactam antibiotics. Chloramphenicol and aminoglycosides inhibit protein synthesis by interacting with the ribosome.

According to a preferred method said biotic-agent is an enzyme. This enzyme is able to degrade or modify the added anti-bios agent. This enzyme is targeted to the target cell through the antibody present in the A-B complex, resulting in the resistance of the target cell towards the anti-bios agent. Several enzymes are known to be able to catalyse the chemical transformation of an anti-bios agent into an inactive form. The well known β-lactamases are enzymes capable of inactivating the penicillins and cephalosporins by cleaving the amide bond of the β-lactam ring common to these antibiotics. Other antibiotics such as chloramphenicol or aminoglycosides can be inactivated by specific enzymes which catalyse the coupling between the anti-bios agent and a chemical group such as an acetyl, a phosphoryl or a nucleotidyl group. The modified anti-bios is inactive.

According to a preferred embodiment the biotic agent is chosen from the group comprising β-lactamases, chloramphenicol-acetyltransferases, aminoglycoside-N-acetyl-transferases, aminoglycoside-O-nucleotidyltransferases, aminoglycoside-O-phosphotransferases. The β-lactamases are known to be able to degrade the β-lactam antibiotics (such as penicillin) eliminating in such a way the selective pressure on the cells. Chloramphenicol-acetyltransferases, aminoglycoside-N-acetyl-transferases, amino glycoside-O-nucleotidyltransferases and aminoglycoside-O-phosphotransferases are known to modify chloramphenicol or aminoglycosides, respectively, by adding a small substituent onto this antibiotic.

According to the present invention the coupling step c of the antibody A with the biotic agent B results in a stable link. If both A and B are polypeptides and the corresponding genes are available, the simplest way to link A and B is to make a gene fusion by linking the DNA coding regions of A and B. To achieve this, the stop codon of the gene encoding A or B has to be replaced by the gene encoding the other polypeptide B or A. A small DNA fragment encoding a spacer peptide can also be genetically inserted between the A and B coding regions in order to allow both A and B polypeptides to fold correctly after expression. The genetic construction is evident for a person skilled in the art. The fusion gene is expressed as a fusion protein A-B and purified using standard protocols. The A-B fusion protein is then used directly as the conjugate in the present invention.

Alternatively, A and B can be linked by a chemical crosslinking reaction. In the preferred embodiment, A and B are polypeptides and contain reactive groups that are susceptible to chemical modification such as amino groups from lysine residues or the amino terminus of the polypeptide, carboxyl groups from the aspartate and glutamate residues and from the carboxy terminus of the polypeptide, and eventually thiol groups from the cysteine residues. As A is an antibody or an antibody derivative, it is generally glycosylated and the glysosyl groups can be oxidised into aldehyde groups. These aldehyde groups are also susceptible to be modified by chemicals. Bifunctional chemicals that are able to react with these reactive groups can be used to crosslink A and B. Bifunctional molecules thus contain two reactive groups that are complementary to, i.e. able to covalently react with, a respective reactive group of A and B.

It will be recognized that virtually any linkage that is stable to the conditions of use and that can be readily formed without denaturing or otherwise degrading the A and/or B may be employed. Suitable groups complementary to the amino reactive groups include, for example, carboxy groups, esters (including activated esters such as NHS-esters), acyl azides, acyl halides, acyl nitriles, aldehydes, alkyl sulfonyl halides, halotriazines, imidoesters, isocyanates, isothlocyanates, sulfonate esters, etc. Suitable reactive groups complementary to the carboxy reactive groups include, for example, amines, alcohols, alkyl halides, thiols, hydrazines, diazoalkanes, sulfonate esters, etc. Suitable reactive groups complementary to the thiol reactive group include, for example, disulfide, maleimide, iodoacetic and iodoacetamido derivatives, etc. Suitable reactive groups complementary to the aldehyde group include, for example, hydrazide. Conditions for forming covalent linkages between a plethora of complementary reactive group pairs are well known. Preferably, each linkage between A and B is an amide. Conditions for linking molecules together having complementary amino and carboxy groups to form amide linkages are well-known (see, e.g., Merrifield 1997 Merrifield, B. 1997. Concept and early development of solid-phase peptide synthesis. Methods Enzymol. 289: 3–13). Specific linking chemistries are provided in the Examples section.

In a preferred embodiment of the invention the covalent linking is promoted using a crosslinker compound chosen from a group comprising glutaraldehyde and maleimide-hydrazide. Glutaraldehyde is a non-specific di-aldehyde cross-linking reagent that reacts with amino groups of the proteins (lysine side chains or amino terminal residues); a site-directed-cross-linking can be performed with maleimide-hydrazide as hydrazide reacts with the oxidised sugar moieties of the antibody and maleimide can react with a cystein residue introduced at the enzyme surface by site directed mutagenesis.

Covalent linkages guarantee that A-B molecules are stable and A does not dissociate from B during the storage and/or while the carrying out of the method. Nevertheless, there exist compounds that have such a very high binding affinity (nanomolar or even higher) for one-another that once they are bound dissociation is negligible and coupling is nearly as stable as found in a covalent linkage. Present inventors also suggests that the coupling step c of the antibody with the biotic agent can promoted using non-covalent binding structures. It is known by a skilled person in the art that streptavidin and avidin has affinity for biotin. Therefore the present invention suggests a possible strategy wherein the antibody and the enzyme are first biotinylated using standard reagents and subsequently associated these indirectly by the addition of streptavidin (or avidin). Streptavidin is a tetrameric protein with an extremely high affinity for biotin allowing the formation of a ternary complex antibody-streptavidin-enzyme. The inventors discuss a specific example wherein the non-covalent linkage of the antibody with the biotic agent is achieved by the biotinylation of both compounds followed by the assembly of both compounds using avidin or streptavidin. This approach of linkage forms a preferred embodiment of the present invention. In a preferred embodiment a conjugate is used as a complex antibody-streptavidine-β-lactamase in the culture medium. The antibody will assure the specificity for the recognition of the bacteria and the resistance to the antibiotic is provided by the use of an enzyme which is in this case β-lactamase which will hydrolize penicilline.

In a preferred method said biotinylation is performed using a reagent chosen from a group comprising biotin-maleimide, biotin-N-hydroxy-succinimide, biotin-hydrazide.

According to the invention, the said supplemented cell mixture is incubated at an optimal growth temperature of the cell to be selected.

In the method according to the invention the subcultured cells obtained at termination of step g are transferred to an antibiotic free rich medium and further incubated to stimulate amplification of the selected cells.

According to the invention the growth or survival of cells is visualized for detection purposes of the selected target cells. With the target cell is meant cells that can be specifically identified from other cell types. Identification can be performed on basis of their protein expression pattern. Cells can be of prokaryotic or eucaryotic origin. From the latter group, cells can be identified being a yeast, fungi, an invertebrate or a vertebrate cell.

In a preferred embodiment of the invention the target cell is a bacterium, preferably chosen from a group of non-pathogenic bacteria comprising *E. coli, Lactobacillus, Streptococci, Bacillus, Pediococci, Streptococci* or chosen from a group of pathogenic bacteria comprising *E. coli* 0-157:H7, *Salmonella, Listeria, Shigella*.

According to the invention, the conjugate compound A-B is composed of a selective antibody or derivative recognizing a target cell A and a biotic agent able to at least partially inactivate an anti-bios agent B. In addition, said anti-bios agent is able to inhibit the growth in the target cell environment.

Preferably, in the conjugate compound A-B the biotic agent B is an enzyme.

According to the invention the conjugate compound A-B can be obtained in several ways.

The present invention also describes a selection medium for cells comprising a conjugate A-B, a corresponding anti-bios agent able inhibit the growth of the mixture of cells and additives stimulating the growth of the target cells.

The present invention also relates to the cells selected using a method according to any method or using a conjugate described of the invention.

The present invention also provides a pharmaceutical compound comprising a conjugate compound A-B for use in the treatment of infectious diseases or cancer or diseases for which protecting healthy cells against an anti-bios agent is wanted such as some autoimmune or genetic diseases. In infectious diseases, pathogenic cells, which are normally not present in the studied part of the organism, are competitive towards endogenous cells. They inhibit or expel the endogenous cells through the depletion of the available resources and/or by blocking the surface that is needed for cell growth. Adding an anti-bios agents which inhibits or repress these pathogenic cells and promoting again the growth of the endogenous cells will help in the cure of the infectious disease. In this case, the compound A-B comprises an antibody or derivative thereof recognising the endogenous cells and does not cross react with the pathogenic cells. In the case of cancer, anti-bios agent is chosen in the group of anticancer drugs. These drugs have usually a toxic effect against some replicating healthy cells. The compound A-B comprises an antibody or derivative thereof recognising these replicating healthy cells and a bios agent capable of inactivating the anticancer drug. Consequently, such a compound can be used to promote healthy cells versus pathogenic or mutated (such as tumor) cells.

The invention also relates to a product or composition comprising the conjugate A-B and the anti-bios agent as a combined preparation for simultaneous, separate or sequential use in the treatment of infectious diseases or cancer or diseases for which protecting healthy cells against an anti-bios agent is wanted.

The present invention also provides a pharmaceutical composition comprising the compound A-B and an anti-bios agent, said anti-bios agent is able to inhibit the growth of cells present in the environment of the target cell. The present invention also relates to the pharmacological composition comprising the compound according to the invention and optionally a pharmaceutical acceptable carrier, diluent or excipient.

These compositions may, for example, be administered parentally or intravenously. The compositions according to the invention for parenteral administration can be, in particular, sterile solutions, aqueous or non-aqueous, suspensions or emulsions, As a pharmaceutically acceptable solution or vehicle propylene glycol, polyethylene glycol, injectable organic esters, for example ethyl oleate, or cyclodextrins may be employed. These compositions can also comprise wetting, emulsifying and/or dispersing agents.

The sterilisation may be carried out in several ways, for example, using bacteriological filter, by incorporating sterilising agents in the composition or by irradiation. They may also be prepared in the form of sterile solid compositions which may be dissolved at the time of use in sterile water or any other sterile injectable medium.

Present invention also involves a kit for the detection of a target cell comprising a first volume of a conjugate as described above and a second volume of a anti-bios agent, said anti-bios agent is able to inhibit the growth of cells.

The present invention also relates to a diagnostic kit comprising a conjugate A-B for the diagnosis of diseases involving organisms of pathogenic sources. Another aspect of the present invention relates to a device for diagnosis and/or assay, comprising the compound according to the invention, especially the compound comprising enzyme substrates which allows fluorescence, chemiluninescence, or colour detection upon activation by the enzyme present in the B moiety of the A-B complex.

The present invention also relates to a product containing a conjugate A-B and a anti-bios agent wherein said anti-bios agent is able to inhibit the growth of cells for simultaneous, separate or sequential use in the therapy of infectious related diseases. The present invention also involves the preparation of a conjugate comprising the following steps: in the case of genetic coupling, the fusion protein A-B is simply expressed, purified and stabilised by additives. For chemical coupling, preparation of the conjugate comprises expression and purification of A and B, dialysis into a buffer allowing the coupling reaction, adding the crosslinking or modifying reagent and incubation until completion, dialysis to remove excess reagent, purification of the conjugate A-B and stabilisation by additives.

The following examples and figure legends merely serve to illustrate the invention and are by no way to be understood as limiting the present invention.

Modes for Carrying Out the Invention

Material and Methods

Solutions Frequently Used:

| | |
|---|---|
| Liquid medium LB: | 20 g LB in one litre milli-Q water and sterilized during 20 minutes in an autoclave. |
| Solid tetracycline medium LB: | 32 g LB dissolved in one litre milli-Q water, sterilized during 20 minutes in an autoclave, 1.5 ml tetracycline 5 mg/ml added and brought in a petri dish. |
| Solid-kanamycine medium LB: | Same as above with the exception that 1 ml kanamycine 50 mg/ml is added before being transferred into the petri dish. |

-continued

| | |
|---|---|
| PBS: | 50 mM NaH$_2$PO$_4$ (m = 3.4498 g) |
| | 100 mM NaCl (m = 2.9220 g) |
| | add to 0.5 litre with milli-Q water and pH adjusted to 7.4. Sterilized during 20 minutes in an autoclave. |
| Biotinylation buffer: | 0.1 M NaHCO$_3$ (m = 16.802 g) |
| | Add 2 litres with milli-Q water and pH adjusted to 8.0. |
| TP (phosphate buffer): | 50 mM K$_2$HPO$_4$ (m = 1.725 g) |
| | Dissolved in 250 ml milli-Q water and pH adjusted to 7.0. Sterilized during 20 minutes in an autoclave. |

Demonstration of the Absence of Release of Infectious Phages by TG1-fd Bla I7

A culture of TG1-fd Bla I7 is centrifuged during 5 minutes at 4000 RPM. The supernatant is recuperated and filtered, then it is introduced into a TG1 culture which is held during 45 minutes at 37° C. without agitation. This culture is incubated during the night at 37° C. with agitation and then a sample is brought in a solid medium with and without tetracycline. These boxes are incubated during the night at 37° C.

Introduction of a Plasmide pET26b45 in MM294

A MM294 culture is centrifuged (5 minutes, 4000 RPM) and the supernatant is eliminated. In an ice bath, the pellet is resolved into 20 ml CaCl$_2$ 50 mM cold (4° C.), then the mixture is centrifuged in the same conditions as above. The supernatant is again eliminated and the pellet is resolved in 2 ml CaCl$_2$ 50 mM cold (4° C.). 2 µl of the plasmide pET26b45 is added to 200 µl of the competent cell solution and the mixture is conserved at 0° C. during 10 minutes. Then the eppendorf is transferred into a bath at 42° during 90 seconds and then reintroduced into the bath at 0° C. during 5 minutes. The mixture is incubated at 37° C. during one hour and then put on boxes (Kan) which are incubated during the night at 37° C.

Biotinylation of the Proteins and Assembling of the Conjugate Complex

150 µl of β-lactamase (35 µM, 1 mg.ml$^{-1}$) and 150 µl antibody (7 µM, 1 mg.ml$^{-1}$) are separately introduced in dialyse cassettes, which are emerged into 2 litres biotinylation buffer during the night. The content of the cassette is used; adding 1.5 µl biotinecaproïque-succinimide to the antibody (7 mM), and 1.5 µl to the β-lactamase (35 mM). Reaction is made during two hours at environment temperature, then all proteins are introduced into the new dialyse cassette. These are emerged in two litres PBS during six hours, then for the night in a new solution.

The coupling of the biotinylated β-lactamase and antibodies is made by use of streptavidine. 50 µl of the two biotinylted proteins are mixed and every ten minutes 10.4 µl streptavidine (15.2 µM) is added, and this for four consecutive times. This ternary complex solution is conserved at 4° C.

Activity Measurement of β-lactamase

The β-lactamase solution is diluted for 100 times in PBS. 10 µl of the solution is diluted in 1.990 ml of a 0.5 mM penicilline solution (dilution of the β-lactamase: 20.000). The speed is measured of the decrease in optical density at 232 nm, which allows calculation of the activity of the β-lactamase solution.

Nitrocefine Tests

Separately 1 ml OD=1 of TG1-fd Bla I7 and MM294-pET26b45 is centrifuged at 4000 RPM during 5 minutes. Twice the pellet is washed with 1 ml LB and 2 µl of the concentrated ternary complex is added. Rest during one hour at 37° C. and every 15 minutes slight agitation is performed. Again centrifuged (4000 RPM, 5 minutes) with sterile PBS. Finally in 100 µl nitrocefine solution is resolved. Observation is made of the colour evolution.

Nitrocefine solution: 1 mg nitrocefine dissolved in 100 µl DMSO then 1.9 ml TP 50 mM at pH=7.0 is added (yellow coloration).

Spectrometrical Follow Up of the Cultures

Cultures (15 ml, OD=1) of TG1-fd Bla I7 and of MM294-pET26b45 are centrifuged (4000 RPM, 5 minutes). The pellet is washed twice with LB and is resolved in 15 ml sterile LB. In all cases 1 ml of the culture is diluted in 9 ml LB (11 erlenmeyers). Then the necessary quantity of the triple complexes calculated for complete degradation of the penicillin in two hours incubation is added and inbucated one hour at 37° C. Then penicillin is introduced at the final concentrations as indicated in the table below and for two hours at 37° C.

| Number of the erlenmeyer | triple complex | [penicillin] (mg · L$^{-1}$) |
|---|---|---|
| 1 | − | 0 |
| 2 | − | 50 |
| 3 | + | 50 |
| 4 | − | 100 |
| 5 | + | 100 |
| 6 | − | 200 |
| 7 | + | 200 |
| 8 | − | 400 |
| 9 | + | 400 |
| 10 | − | 800 |
| 11 | + | 800 |

A sample is made at the start and then every 30 minutes. The optical density is measured of the sample at 600 nm.

Experiments of the Selected Cultures 5 ml (OD=1) of the TG1-fd Bla I7 and the MM294-pET26b45 cultures are centrifuged (4000 RPM, 5 minutes) and twice washed in LB for finally being resolved in 5 ml sterile LB. Two cultures are mixed. 1 ml of this culture is diluted in 9 ml LB (5 erlenmeyers in parallell) and the necessary quantity of the ternary complex or the conjugate is added. During one hour at 37° C. incubation takes place whereafter penicilline is introduced in this culture medium (see table above) and agitation is performed during two hours at 37° C.

| Number of the erlenmeyer | triple complex | [penicilline] (mg · L$^{-1}$) |
|---|---|---|
| 1 | − | 0 |
| 2 | − | 200 |
| 3 | + | 200 |
| 4 | − | 800 |
| 5 | + | 800 |

Sampling is made at the start and the finish of the reaction which is diluted and put on Tet or Kan boxes. The incubation takes place all night at 37° C. Calculation of the colonies is made the morning after.

Results

The method was performed using the non-pathogenic model organism *Escherichia coli* (*E. coli*). This is a Gram negative bacteria which is frequently used in laboratories. It is however clear that a main focus of the invention is the detection of pathogenic bacteria but for reasons of security in the experiments non-pathogenic bacteria are used.

The bacterial strain *E. coli* which is used (TG1) possesses episome F' and can be infected by a filamentous phage (e.g.

are M13, fl and fd). These filamentous phages are viruses capable of infecting Gram negative bacteria without killing it (phages are budding). Generally, these phages consists of a DNA strand surrounded by a protein envelope wherein the pVIII protein is the most prominent one. The infection of E.coli by bacterial phages is initiated by interaction of protein pIII with sexual pilus F of strain F$^+$ of the bacteria. Proteins necessary for the formation of this pilus are expressed from the F-episome. The DNA of the phage is then injected and replicated by the bacteria. Subsequently the phage genes are expressed in the cell, followed by the assembly of the phage coat proteins (pVII, pIX, pVIII, pIII and pVI) at the bacterial cell membrane.

As reference strain *E. coli* MM294 which does not possess the episome F' and consequently can not be infected by the phages is used.

All bacteria used in the experiments are sensible to the antibiotic penicillin. Within the antibody-enzyme conjugate A-B B is preferentially β-lactamase; as anti-bios agent penicillin (ampicillin) is preferred. The β-lactamase cleaves the β-lactam group of the penicillin resulting in the inactivation of the antibiotic (see FIG. 1).

The antibody (A) used within the antibody-enzyme conjugate A-B recognises the phage pVIII-protein which is expressed on the surface of the phage.

Characterisation of the used Bacteria TG1-fd Bla I7

TG1-fd Bla I7 is an *E. coli* TG1 strain transformed by a non-infectious phage fd Bla I7 (kindely provided by D. Legendre). This phage is a non-infectious variant and is characterised by the premature termination of the reading frame coding for one of the coat proteins pIII. The absence of the pIII protein results in phages that stay associated with the infected bacteria. Therefore, the target bacteria TG1-fd Bla I7 is a bacteria covered with phages (hair like) and, as the main coat protein of the phages is pVIII, the antibody (A) will be recognising the surface of that bacteria. fd Bla I7 also carries a marker of resistance for antibiotic tetracycline which makes it possible to make an inventory how many bacteria are transformed with this fd phage.

In order to test the non-infectious state of the phage, a culture of TG1-fd Bla I7 was centrifuged and the supernatant recovered and filtrated to eliminate any remaining bacteria. Part of this supernatant was added to a culture of TG1 cells. Subsequently, this cell suspension was plated out on tetracyclin-containing-bacterial growth plates and incubated overnight at 37° C. As expected, no colony has been observed proving that TG1-fd Bla I7 could not produce an infectious phage are confirming that these phages are non-infectious.

It was also observed that the bacteria TG1, when transformed by phage fd BlaI7, multiplies in a smaller rate compared to the wild type TG1 strain (not transformed) (see FIG. 2). This observation indicates that the phage transformation causes a low toxicity effect on the TG1 bacteria.

Transformation of MM294 by pET26b45

The control strain, MM294, does not show resistance to any of the frequently used antibiotics, this in contrast to TG1-fd Bla I7 which carries resistance to tetracycline. In order to make it easy to follow the presence of both strains, there was a need for making MM294 resistant to an antibiotic other than tetracycline. For this purpose resistance to kanamycin was chosen. This was obtained by transforming MM294 using the thermal shock method as known by a skilled person in the art with a plasmide (pET26b45) carrying the resistant gene to kanamycin. It was additionally tested that the transformed bacteria were capable to grow in the presence of Kanamycin (KM) and not in the presence of Tetracyclin (Tet). It is this kanamycine resistant strain (MM294-pET26b45) that will be used as a negative reference for the test as MM294 is not producing phages and is therefore not recognised by the antibody.

In this way, the presence of both strains can be easily followed by growing the suspension in selective media, e.g. on selective plates containing Tetracycline or Kanamycin respectivey thereby inhibiting one of both strains and promoting the growth of the other depending of the antibiotic added. So mixtures of TG1-fd Bla I7 (Tet') and MM294 (KM') can be easily made and tested for growth.

Construction of the Conjugate

The construction of the conjugate complex antibody-streptavidine-β-lactamase is performed in two steps: in a first step the antibody and β-lactamase are biotinylated and in a second step the biotinylated proteins are assembled by streptavidine.

Biotinylation of the Proteins

First the antibody and the β-lactamase are dialysed in order to transfer both in a buffer necessary for the biotinylation. Secondly, the substitution of the two proteins was promoted using biotine-caproïque-succinimide as elucidated in the FIG. 5. This succinimide reacts with the lysine groups that are found on the surface of the proteins.

After this chemical transformation of proteins the activity of β-lactamase was tested to find out if this transformation resulted in the loss of enzymatic activity. Indeed, tests showed that 22% of the β-lactamase activity was lost during biotinylation. In addition, the purity of the proteins was analysed. This was performed by running samples on an acrylamide SDS-PAGE (12% gel) and results confirmed that the obtained proteins were pure.

Formation of the Conjugate

The antibody and the biotinylated β-lactamase were introduced in a micro-tube in which progressively streptavidine is added. Streptavidine has four binding sites for biotine and thus possess a high affinity towards both biotinylated proteins.

In order to verify the production of the conjugate a nitrocefine test was performed. Hereby a yellow colored substrate for the β-lactamase enzyme, Nitrocefine, was used. When β-lactamase is active and combined with its substrate nitrocefine, the β-lactam-structure of nirtrocefine gets cleaved. This changes the yellow colored substrate to a red colored hydrolysed product. This is shown in FIG. 6. The inventors tested if target bacteria could be colored depending on the presence of the β-lactamase enzyme on their surface. In a first step washed bacteria are brought into contact with the described ternary complex (conjugate A-B). After a second wash, where the excess of the complex was eliminated, cells were a resuspended in a nitrocefine solution. In this way, bacteria could be discriminated from each other by their color: the suspension of TG1-fd Bla I7 is colored red, MM294-pET26b45 remains yellow. We therefore demonstrated that the β-lactamase is fixed on bacteria TG1-fd Bla I7 via the binding of the ternary complex anti-pVII-streptavidine-β-lactamase (conjugate A-B) onto the surface of the bacteria.

Spectrophotometric Proof of the Growth

In the next step, the applicant determined the conditions where optimal measurements could be made. With the help of spectrophotometric techniques the evolution in the optical density of different cultures was followed. Four cell suspension were made as described below and tested for their optical density:

MM294-pET26b45 without ternary complex (conjugate A-B)

MM294-pET26b45 with ternary complex (conjugate A-B)

TG1-fd Bla 17 without ternary complex (conjugate A-B)

TG1-fd Bla 17 with ternary complex (conjugate A-B).

These cultures were made in parallel with an increasing concentration of penicillin increasing in the culture medium from 0 mg.L$^{-1}$, 50 mg.L$^{-1}$, 100 mg.L$^{-1}$, 200 mg.L$^{-1}$, 400 mg.L$^{-1}$ to 800 mg.L$^{-1}$. The quantities of the ternary complex were calculated and adapted such that all the penicillin in the medium of culture were hydrolyzed in two hours. The obtained results are elucidated hereunder in FIG. 5.

From these results we have concluded to perform further tests with concentrations 200 and 800 mg.L$^{-1}$ of penicillin. In these conditions cultures of MM294-pET36b45 (with and without triple complex) and cultures of TG1-fd Bla I7 without ternary complex have an optical density which has the tendency to decrease during time instead the TG1-fd Bla I7 in the presence of the complex which increases. We assume a correlation with optical density and the bacteria concentration in the culture medium.

Experiments with Selective Cultures

Mixtures have been made of bacteria TG1-fd Bla I17 and MM294-pET26b45. These mixtures have been brought into contact with the ternary complex and incubated during one hour by 37° C. to allow the triple complex to be formed on the bacteria. After this incubation penicillin is added in the culture medium and cultures grown in shaking suspensions for two hours at 37° C. Subsequently, these mixtures were plated on Tet dishes and Kan dishes and incubated overnight at 37° C. The next day, the number of colonies was counted. The results thereof are mentioned in table 1.

The inventors have also been working on the optimisation of the initial number added in the test of the different bacteria. Results of the experiments are shown in table 2. The results showed only a selective protection of the bacteria TG1-fd Bla I7 in relation to the bacteria MM294-pET26b45 in the presence of the ternary complex could be obtained.

Conclusion

The inventors could conclude that assembling the conjugate antibody-streptavidine-β-lactamase is possible and that both the epitope recognition and the lactamase activity are preserved. In addition, inventors showed that a selective protection of bacteria TG1-fd Bla I7 is possible towards the non-protected bacteria MM294-pET26b45 using this antibody-streptavidine-β-lactamase conjugate. The inventors could find in some cases selective amplification of the target bacteria.

References

Rakonjac J, Model P. Roles of pIII in filamentous phage assembly. *J Mol Biol.* 1998; 282: 25–41.

Matagne A, Lamotte-Brasseur J, Frere J M. Catalytic properties of class A beta-lactamases: efficiency and diversity. *Biochem J.* 1998; 330: 581–98.

Russell A D. Mechanisms of bacterial resistance to antibiotics and biocides. *Prog Med Chem.* 1998; 35: 133–97.

Sutherland I W. Biosynthesis and composition of gram-negative bacterial extracellular and wall polysaccharides. *Annu Rev Microbiol.* 1985; 39: 243–70.

Beveridge T J. Ultrastructure, chemistry, and function of the bacterial wall. *Int Rev Cytol.* 1981; 72: 229–317.

Werlen R C, Offord R E, Blakey D C, East S J, Melton R G, Rose K. In vitro and in vivo comparison of a randomly coupled antibody fragment-enzyme conjugate with a site-specific conjugate. *Biomed Pept Proteins Nucleic Acids.* 1995; 1: 251–4.

Werlen R C, Lankinen M, Rose K, Blakey D, Shuttleworth H, Melton R, Offord R E. Site-specific conjugation of an enzyme and an antibody fragment. *Bioconjug Chem.* 1994; 5: 411–7.

TABLE 1

Demonstration of the selective protection of TG1-fd Bla I7 compared to MM294-pET26b45 by adding a conjugate β-lactamase-antibody (complex) and penicillin G (Pen) as anti-bios agent. After two hours, the percentage of TG1-fd Bla I7 cells increases only when the conjugate is added.

| Time | Bacteria.ml$^{-1}$ | | % TG1-fd |
|---|---|---|---|
| results 1 | TG1-fd Bla 17 | MM294-pET26b45 | Bla 17 |
| t = 0 | 1.58E+06 | 6.00E+06 | 20.8% |
| t = 2 hours | | | |

| [Pen] (mg · L$^{-1}$) | Complex | | | |
|---|---|---|---|---|
| 0 | − | 2.98E+07 ppm | 8.52E+07 ppm | 8.4% |
| 200 | − | 1 190 ppm | 1 667 ppm | 15.8% |
| 200 | + | 734 177 ppm | 108 000 ppm | 64.2% |
| 800 | − | 1 500 ppm | 557 ppm | 8.9% |
| 800 | + | 69 620 ppm | 36 000 ppm | 33.7% |

TABLE 2

Demonstration of the selective protection of TG1-fd Bla I7 compared to MM294-pET26b45 by adding a conjugate β-lactamase-antibody (complex) and penicillin G (Pen) as anti-bios agent. After two hours, the percentage of TG1-fd Bla I7 cells increases only when the conjugate is added.

| | Bacteria.ml$^{-1}$ | | % TG1-fd |
|---|---|---|---|
| Time | TG1-fd Bla I7 | MM294-pET26b45 | Bla I7 |
| results 1 | | | |
| t = 0 | 2.05E+07 | 1.73E+07 | 54.2% |
| t = 2 hours | | | |

| [Pen] (mg · L$^{-1}$) | Complex | | | |
|---|---|---|---|---|
| 200 | − | 351.2 ppm | 410.4 ppm | 50.3% |
| 200 | + | 110243.9 ppm | 9132.9 ppm | 93.5% |
| 800 | − | 439.0 ppm | 659.0 ppm | 44.1% |
| 800 | + | 5756.1 ppm | 711.0 ppm | 90.6% |
| results 2 | | | | |
| t = 0 | | 1.37E+08 | 9.00E+07 | 60.4% |
| t = 2 hours | | | | |

| [Pen] (mg · L$^{-1}$) | Complex | | | |
|---|---|---|---|---|
| 0 | − | 1.55E+06 ppm | 8.00E+06 ppm | 22.8% |
| 200 | − | 48.2 ppm | 82.2 ppm | 47.1% |
| 200 | + | 12992.7 ppm | 2266.0 ppm | 89.7% |
| 800 | − | 2.9 ppm | 60.0 ppm | 6.9% |
| 800 | + | 1445.3 ppm | 1477.8 ppm | 59.8% |

What is claimed is:

1. A method for the selective survival or selective growth of a bacterial target cell comprising the steps of:
    a) contacting the bacterial target cell with a conjugate compound A-B, wherein A is a selective antibody or antibody derivative recognizing the target cell and B is an enzyme able to inactivate an antibiotic, wherein said antibiotic inhibits the growth of the bacterial target cell; and
    b) contacting the bacterial target cell with the antibiotic;

wherein said antibiotic is a β-lactam antibiotic, chloramphenicol, or an aminoglycoside, and/or wherein the enzyme is a β-lactamase, a chloramphenicol-acetyltransferase, an aminoglycoside-N-acetyltransferase, an aminoglycoside-O-nucleotidyltransferase, or an aminoglycoside-Q-phosphotransferase.

2. The method according to claim 1, wherein steps a) and b) are performed sequentially.

3. The method according to claim 1, wherein steps a) and b) are performed simultaneously.

4. The method according to claim 1, wherein the bacterial target cell is selected from a mixture of cells and the antibiotic is able to inhibit the growth of the mixture of cells.

5. The method according to claim 2, wherein the target cells are cultivated and detected after step b).

6. A method for the selective survival or selective growth of a bacterial target cell from a mixture of cells comprising the steps of:
 a) identifying a selective antibody or antibody derivative A recognizing the target cell from a mixture of cells,
 b) identifying an antibiotic able to inhibit the growth of the mixture of cells containing the target cell and a corresponding enzyme B able to at least partially inactivate the antibiotic,
 c) coupling the antibody A with the enzyme B chosen in steps a) and b) resulting in a conjugate A-B,
 d) preparing a medium containing the conjugate A-B,
 e) bringing together the mixture of cells of step a) with the medium obtained in step d),
 f) adding the antibiotic to the medium obtained in step e), and
 g) incubating the medium obtained in step f);
wherein said antibiotic is a β-lactam antibiotic, chloramphenicol, or an aminoglycoside, and/or wherein the enzyme is a β-lactamase, a chloramphenicol-acetyltransferase, an aminoglycoside-N-acetyltransferase, an aminoglycoside-O-nucleotidyltransferase, or an aminoglycoside-O-phosphotransferase.

7. The method according to claim 6, wherein said antibiotic is a β-lactam antibiotic, chloramphenicol, or an aminoglycoside.

8. The method according to claim 6, wherein the enzyme is a β-lactamase, a chloramphenicol-acetyltransferase, an aminoglycoside-N-acetyltransferase, an aminoglycoside-O-nucleotidyltransferase, or an aminoglycoside-O-phosphotransferase.

9. The method according to claim 6 wherein the coupling step c) results in a covalent link.

10. The method according to claim 9 wherein the covalent linking is promoted using a crosslinker compound selected from the group consisting of glutaraldehyde and maleimide-hydrazide.

11. The method according to claim 6 wherein the coupling step c) results in a non-covalent link.

12. The method according to claim 11 wherein the non-covalent linking is achieved by a) biotinylation of the antibody and the enzyme, respectively, and b) assembly of the biotinylated antibody and the biotinylated enzyme on avidin or streptavidin.

13. The method according to claim 12 wherein said biotinylation is performed using a reagent selected from the group consisting of biotin-maleimide, biotin-N-hydroxysuccinamide, and biotin-hydrazide.

14. The method according to claim 6 wherein the medium in step f) is incubated at an optimal growth temperature of the cell to be selected.

15. The method according to claim 6 further comprising subculturing cells after step g) to obtain subcultured cells, and said subcultured cells are transferred to an antibiotic free rich medium and further incubated to stimulate amplification of the subcultured cells.

16. The method according to claim 6 wherein growth or survival of cells is visualized to detect the selected target cells.

17. The method according to claim 6 wherein the bacterial target cell is a non-pathogenic E. coli, a Lactobacillus, a Streptococcus, a Pediococcus, E. coli 0-157:H7, a Salmonella, a Listeria, or a Shingella.

18. The method according to claim 1, wherein said antibiotic is a β-lactam antibiotic, chloramphenicol, or an aminoglycoside.

19. The method according to claim 1, wherein the enzyme is a β-lactamase, a chloramphenicol-acetyltransferase, an aminoglycoside-N-acetyltransferase, an aminoglycoside-O-nucleotidyltransferase, or an aminoglycoside-O-phosphotransferase.

20. The method according to claim 1 wherein the bacterial target cell is a non-pathogenic E. coli, a Lactobacillus, a Streptococcus, a Pediococcus, E. coli 0-157:H7, a Salmonella, a Listeria, or a Shingella.

21. The method according to claim 1, wherein the antibiotic is a β-lactam antibiotic.

22. The method of claim 1, wherein the target cell is an E. coli.

23. The method according to claim 1, wherein the antibiotic is a β-lactam antibiotic and the target cell is an E. coli.

24. The method according to claim 6, wherein the antibiotic is a β-lactam antibiotic.

25. The method according to claim 6, wherein the target cell is an E. coli.

26. The method according to claim 6, wherein the antibiotic is a β-lactam antibiotic and the target cell is an E. coli.

* * * * *